(12) United States Patent
Humphrey et al.

(10) Patent No.: US 6,444,680 B1
(45) Date of Patent: Sep. 3, 2002

(54) AMINE SALTS OF AN INTEGRIN RECEPTOR ANTAGONIST

(75) Inventors: Guy R. Humphrey, Hillsborough; Marjorie See Waters, Cranbury, both of NJ (US); Wei Xu, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/998,416

(22) Filed: Nov. 29, 2001

Related U.S. Application Data

(60) Provisional application No. 60/250,268, filed on Nov. 30, 2000.

(51) Int. Cl.[7] .................. C07D 401/14; A61K 31/14; A61K 31/4375
(52) U.S. Cl. ........................ 514/256; 544/333
(58) Field of Search ............................ 544/333; 514/256

(56) References Cited

U.S. PATENT DOCUMENTS 6,048,861 A * 4/2000 Askew et al. ............... 544/333

FOREIGN PATENT DOCUMENTS

WO WO99/31061 6/1999

\* cited by examiner

*Primary Examiner*—John M. Ford
(74) *Attorney, Agent, or Firm*—Philippe L. Durette; Melvin Winokur

(57) ABSTRACT

Amine salts of 3-(2-methyl-pyrimidin-5-yl)-9-(5,6,7,8-tetrahydro-[1,8]-naphthyridin-2-yl)-nonanoic acid are potent antagonists of the integrin $\alpha v \beta 3$ receptor and are useful for the prevention and/or treatment of osteoporosis and vascular restenosis, as well as conditions associated with excessive angiogenesis, such as macular degeneration, diabetic retinopathy, atherosclerosis, inflammatory arthritis, cancer, and metastatic tumor growth. The invention also relates to a process for the preparation of the novel salts as well as pharmaceutical compositions containing the salts and methods of using the salts. Also disclosed are 3(R)- and 3(S)-(2-methylpyrimidin-5-yl)-9-(5,6,7,8-tetrahydro-[1,8] naphthyridin-2-yl)-nonanoic acid in the form of a zwitterion trihydrate.

15 Claims, 12 Drawing Sheets

AMINE SALTS OF AN INTEGRIN RECEPTOR ANTAGONIST

This application claims the benefit of U.S. Provisional Application No. 60/250,268, filed Nov. 30, 2000.

FIELD OF THE INVENTION

The present invention relates to particular salts of an integrin receptor antagonist. More particularly, the invention relates to amine salts of 3-(2-methyl-pyrimidin-5-yl)-9-(5,6,7,8-tetrahydro-[1,8]-naphthyridin-2-yl)-nonanoic acid, which are potent integrin $\alpha_v\beta_3$ receptor antagonists. These novel salts are therefore useful for the treatment and prevention of diseases and conditions for which an antagonist of the integrin $\alpha_v\beta_3$ receptor is indicated.

BACKGROUND OF THE INVENTION

Integrin $\alpha_v\beta_3$ receptor antagonists have been described as being of use for the prevention and/or treatment of osteoporosis, vascular restenosis, macular degeneration, diabetic retinopathy, atherosclerosis, inflammatory arthritis, cancer, and metastatic tumor growth [see, for example, M. E. Duggan, et al., "Ligands to the integrin receptor $\alpha_v\beta_3$, *Exp. Opin. Ther. Patents*, 10: 1367–1383 (2000); M. Gowen, et al., "Emerging therapies for osteoporosis," *Emerging Drugs*, 5: 1–43 (2000); J. S. Kerr, et al., "Small molecule $\alpha_v$ integrin antagonists: novel anticancer agents," *Exp. Opin. Invest. Drugs*, 9: 1271–1291 (2000); and W. H. Miller, et al., "Identification and in vivo efficacy of small-molecule antagonists of integrin $\alpha_v\beta_3$ (the vitronectin receptor)," *Drug Discovery Today*, 5: 397–408 (2000)].

U.S. Pat. No. 6,048,861, assigned to Merck & Co., describes a class of 9-substituted-3-aryl-nonanoic acid derivatives, which are potent integrin $\alpha_v\beta_3$ receptor antagonists and therefore useful for inhibiting bone resorption, vascular restenosis, treating and/or preventing osteoporosis, and inhibiting diseases and conditions associated with excessive and undesirable angiogenesis. Specifically disclosed in U.S. Pat. No. 6,048,861 is 3-(2-methyl-pyrimidin-5-yl)-9-(5,6,7,8-tetrahydro-[1, 8]-naphthyridin-2-yl)-nonanoic acid. Pharmaceutically acceptable salts of this compound are generically encompassed within the scope of U.S. Pat. No. 6,048,861.

However, there is no specific disclosure in the above reference of the newly discovered amine salts of 3-(2-methyl-pyrimidin-5-yl)-9-(5,6,7,8-tetrahydro-[1,8]-naphthyridin-2-yl)-nonanoic acid of structural formula I below.

SUMMARY OF THE INVENTION

This invention provides new amine salts of 3-(2-methyl-pyrimidin-5-yl)-9-(5,6,7,8-tetrahydro-[1,8]-naphthyridin-2-yl)-nonanoic acid of the following structural formula I:

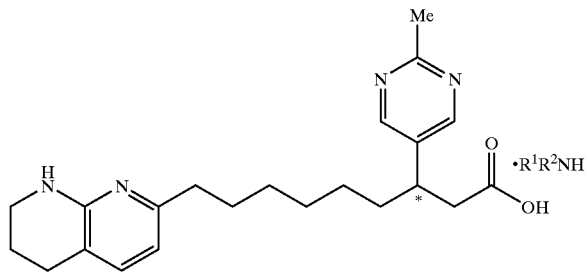

(I)

or a pharmaceutically acceptable solvate, including hydrate, thereof, wherein $R^1$ and $R^2$ are both hydrogen, $R^1$ is hydrogen and $R^2$ is $C(CH_2OH)_3$, $R^1$ is hydrogen and $R^2$ is $C(CH_3)_2CH_2OH$, $R^1$ is hydrogen and $R^2$ is $CH_2CH_2NH_2$, or $R^1$ is $CH_2C_6H_5$ and $R^2$ is $CH_2CH_2C_6H_5$.

The amine salts of the present invention have a chiral center (indicated with an \*) at the C-3 position of the nonanoic acid chain and can thus occur as a racemate, racemic mixture, and single enantiomers, with all isomeric forms being included in the present invention. The separate enantiomers, substantially free of the other, are included within the scope of the invention, as well as mixtures of the two enantiomers.

Therefore, one embodiment of the present invention provides the amine salts of 3(S)-(2-methyl-pyrimidin-5-yl)-9-(5,6,7,8-tetrahydro-[1,8]-naphthyridin-2-yl)-nonanoic acid of structural formula II:

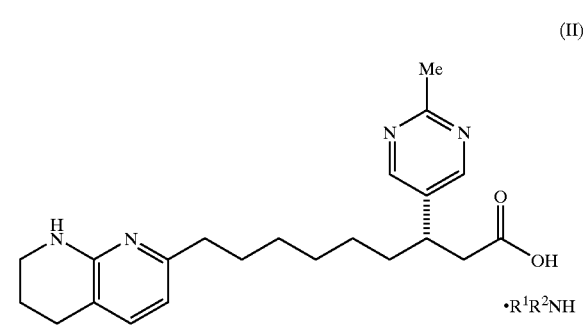

(II)

wherein $R^1$ and $R^2$ are both hydrogen, $R^1$ is hydrogen and $R^2$ is $C(CH_2OH)_3$, $R^1$ is hydrogen and $R^2$ is $C(CH_3)_2CH_2OH$, $R^1$ is hydrogen and $R^2$ is $CH_2CH_2NH_2$, or $R^1$ is $CH_2C_6H_5$ and $R^2$ is $CH_2CH_2C_6H_5$.

A second embodiment of the present invention provides the amine salts of 3(R)-(2-methyl-pyrimidin-5-yl)-9-(5,6,7,8-tetrahydro-[1,8]-naphthyridin-2-yl)-nonanoic acid of structural formula III:

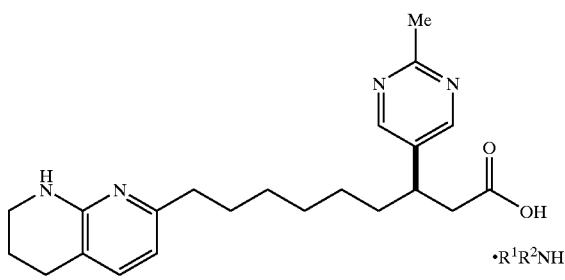

(III)

wherein
- $R^1$ and $R^2$ are both hydrogen,
- $R^1$ is hydrogen and $R^2$ is $C(CH_2OH)_3$,
- $R^1$ is hydrogen and $R^2$ is $C(CH_3)_2CH_2OH$,
- $R^1$ is hydrogen and $R^2$ is $CH_2CH_2NH_2$, or
- $R^1$ is $CH_2C_6H_5$ and $R^2$ is $CH_2CH_2C_6H_5$.

More specifically, the amine salts of the present invention are comprised of one molar equivalent of 3-(2-methyl-pyrimidin-5-yl)-9-(5,6,7,8-tetrahydro-[1,8]-naphthyridin-2-yl)-nonanoic acid anion and one molar equivalent of ammonium ($R^1=R^2=H$) cation, protonated ethylenediamine cation ($R^1=H$, $R^2=CH_2CH_2NH_2$), protonated 2-amino-2-methyl-1-propanol cation [$R^1$=hydrogen, $R^2=C(CH_3)_2CH_2OH$], protonated tris(hydroxymethyl)aminomethane cation [$R^1$=hydrogen, $R^2=C(CH_2OH)_3$], or protonated N-benzyl-2-phenethylamine cation ($R^1=CH_2C_6H_5$, $R^2=CH_2CH_2C_6H_5$).

In a further embodiment of the present invention, the amine salts of structural formulae I–III are crystalline.

The crystalline amine salts of structural formula I exhibit greater chemical and physical stability than the parent zwitterionic compound of structural formula (IV) below. These salts are therefore more desirable for the preparation of solid pharmaceutical dosage forms containing the pharmacologically active ingredient.

The amine salts of the present invention, which exhibit potent integrin $\alpha_v\beta_3$ antagonist activity, are particularly useful for inhibiting bone resorption, treating and/or preventing osteoporosis, and inhibiting vascular restenosis, diabetic retinopathy, macular degeneration, atherosclerosis, inflammatory arthritis, cancer, and metastatic tumor growth.

Another aspect of the present invention provides compounds 2–6a and 2–6b in the form of a zwitterion trihydrate.

DETAILED DESCRIPTION OF THE INVENTION

Figure 1:
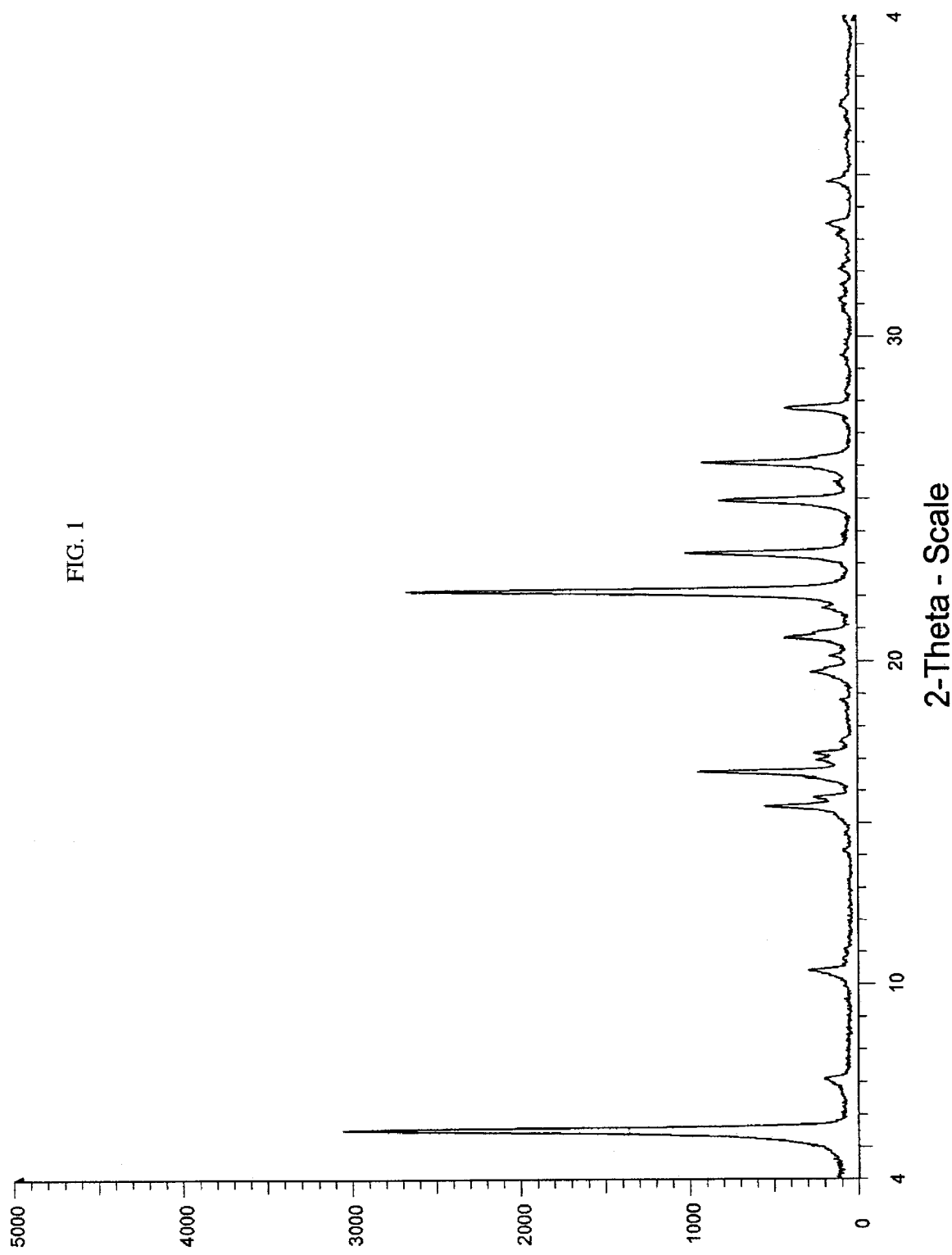
FIG. 1 is a characteristic X-ray diffraction pattern of the crystalline salt of structural formula I wherein $R^1$ is hydrogen and $R^2$ is $C(CH_2OH)_3$.

The present invention provides a pharmaceutical composition comprising the amine salts of structural formula I above, or a pharmaceutically acceptable solvate thereof, in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remingon's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, the salt of the present invention may be administered in a single daily dose, or the total daily dosage may be administered in divided doses of two, three or four times daily. Furthermore, the salt of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the salts herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug component can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

According to a further aspect, the present invention provides a process for the preparation of the amine salts of formula I, which process comprises reacting 3-(2-methyl-pyrimidin-5-yl)-9-(5,6,7,8-tetrahydro-[1,8]-naphthyridin-2-yl)-nonanoic acid of structural formula IV below:

(IV)

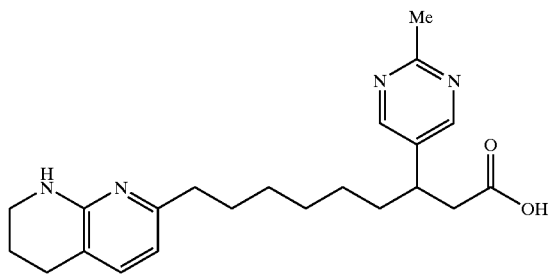

with approximately one molar equivalent of the appropriate $R^1R^2NH$ amine in a suitable organic solvent. The process is carried out generally at about 0° C. to 100° C., and preferably at about 20° to 40° C. Generally, the organic solvent is a linear or branched $C_1$–$C_4$ alkanol, such as methanol, ethanol, or isopropanol, a linear or branched $C_{1-4}$ alkyl acetate, such as ethyl acetate or isopropyl acetate, diethyl ether, toluene, or acetonitrile, or aqueous organic solvent. In one embodiment, the organic solvent is a $C_{1-4}$ alkanol or aqueous $C_{1-4}$ alkanol. Crystallization is then effected by adding a solvent, such as ethyl acetate, and optional seeding with crystals of the authentic amine salt, but the latter is not essential. The amine salts are then isolated and purified by conventional procedures, such as by filtration and drying.

The starting compound of structural formula IV can be prepared by the procedures detailed in Schemes 1–2 and Example 1 below.

In a still further aspect, the present invention provides a method for the treatment and/or prevention of clinical conditions for which an integrin $\alpha v\beta 3$ receptor antagonist is indicated, which method comprises administering to a patient in need of such prevention or treatment a prophylactically or therapeutically effective amount of the salt of structural formula I as defined above or a pharmaceutically acceptable solvate thereof.

The present invention also provides the use of a salt of structural formula I as defined above or pharmaceutically acceptable solvate thereof for the manufacture of a medicament for the prevention and/or treatment of clinical conditions for which an antagonist of the integrin $\alpha v\beta 3$ receptor is indicated.

Another aspect of the present invention provides compounds 2–6a and 2–6b in the form of a zwitterion trihydrate.

The following non-limiting Examples are intended to illustrate the present invention and should not be construed as being limitations on the scope or spirit of the instant invention.

All X-ray patterns were obtained on a Siemens D5000 X-ray diffractometer, using Cu $K\alpha$ radiation. All DSC thermograms were taken on a TA 2920 Differential Scanning Calorimeter with a heating rate of 10° C./minute under nitrogen. The carbon-13 CPMAS nuclear magnetic resonance (NMR) spectra were collected with a 200 MHz Varian Inova solid-state NMR spectrometer; a contact time of 1.5 seconds and a pulse delay of 5 seconds were used for all samples. The FT-infrared spectra were obtained using a Perkin Elmer FT-IR Spectrum One spectrometer; spectra were collected at 4 $cm^{-1}$ resolution.

Scheme 1

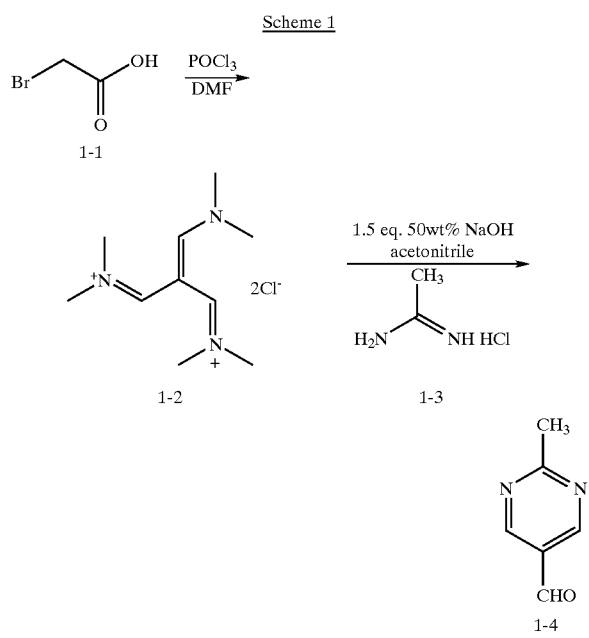

Scheme 2
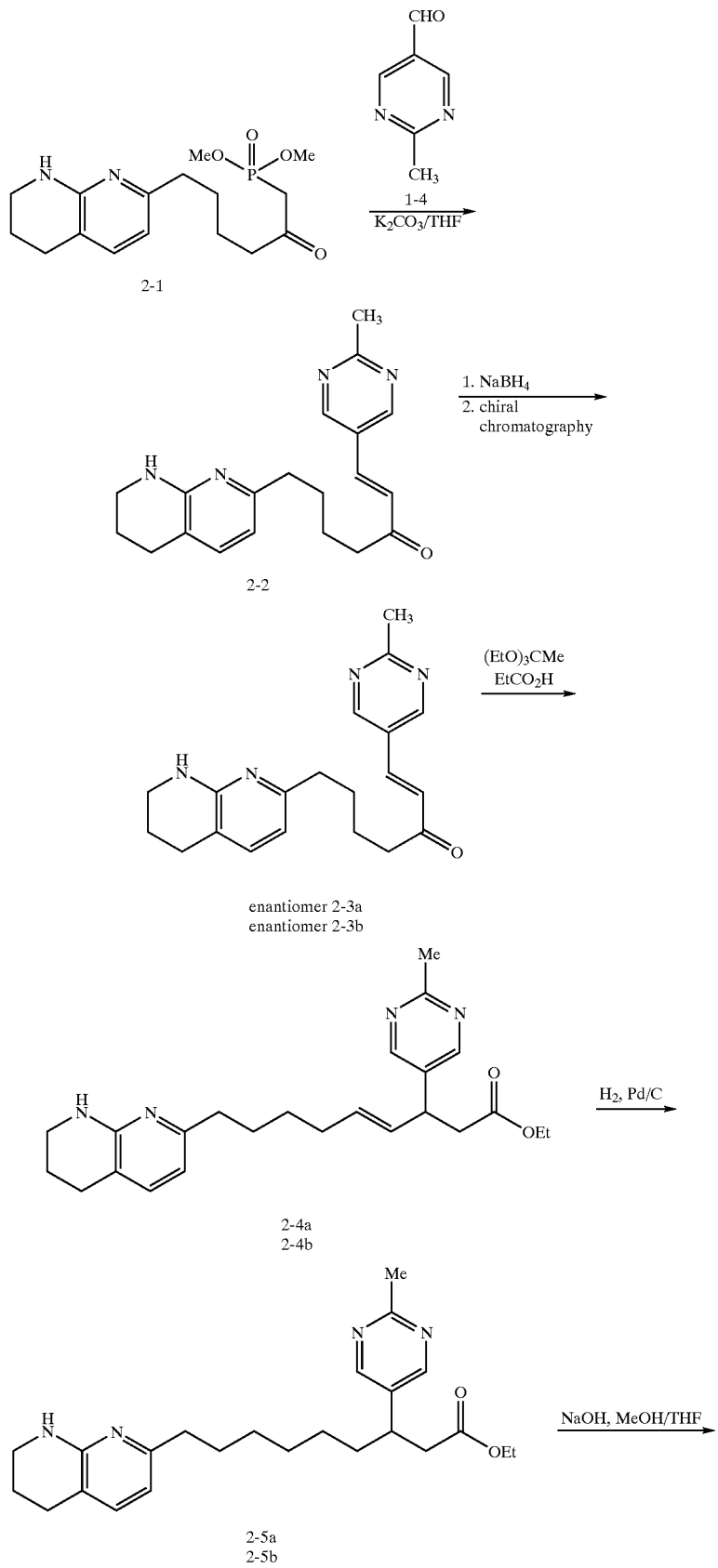

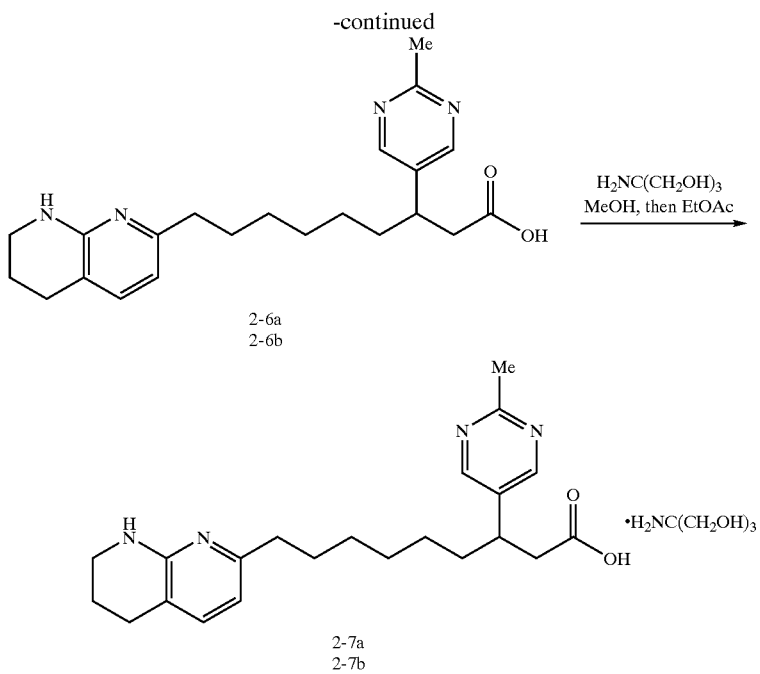

2-6a
2-6b 2-7a
2-7b

Step A: Preparation of 2-methyl-pyrimidine-5-carboxaldehyde (1–4)

To a solution of bromoacetic acid 1-1 (12 g, 86.4 mmol) in DMF (44 mL) at 90° C. was added phosphorous oxychloride (24 mL, 260 mmol) over 5 h and then heated to 110° C. After stirring at 110° C. for 2.5 h, the mixture was cooled to 45° C. and quenched into cold isopropanol (44 mL) at 2° C. and diluted with isopropyl acetate (44 mL) and then treated with water (6.2 mL), which was added over 45 minutes at 2° C., to form the dichloride vinamidinium salt 1-2. After stirring for 1 h, the deposited solid was collected and washed with isopropyl acetate (2×14 mL) and acetonitrile (2×14 mL) to afford 1-2 (12.0 g, 54%) as a pale yellow crystal.

To a slurried mixture of dichloride vinamidinium salt 1-2 (10.1 g, 39.9 mmole) and acetamidine hydrochloride 1-3 (4.2 g, 44.4 mmol) in acetonitrile (48 mL) at 22° C. was added 50% sodium hydroxide (4.9 g, 61.1 mmol) over 1.5 h and stirred at room temperature for 1.5 h.

The reaction mixture was filtered and washed with acetonitrile (10 mL), and the combined filtrate was concentrated under reduced pressure and solvent switched to heptane. The resulting mixture of crude 1-4 in heptane (25 mL) was extracted with methyl t-butyl ether (MTBE) (4×20 mL) at 40° C. The combined MTBE extracts were filtered through a pad of silica gel and concentrated under reduced pressure. The residue was recrystallized from heptane to give aldehyde 1-4 (2.15 g, 44%) as pale yellow solid; m.p. 78–79° C. $^1$H NMR (400.25 MHz, CDCl$_3$): δ10.09 (s, 1H), 9.03 (s, 2H), 2.79 (s, 3H) ppm. $^{13}$C NMR (100.64 MHz, CDCl$_3$): δ189.0, 173.2, 158.2, 126.3, 26.7 ppm.

Step B: 1-(2-Methylpyrimidin-5-yl)-7-(5,6,7,8-tetrahydro-[1,8]naphthyridin-2-yl)-hept-1-en-3-one (2–2)

A stirred suspension of anhydrous powdered K$_2$CO$_3$ (6.21 g, 45 mmol), ketophosphonate 2-1 (for preparation of 2-1, see U.S. Pat. No. 6,048,861) (7.66 g, 22.5 mmol), and 2-methyl-pyrimidine-5-carboxaldehyde 1-4 (2.5 g, 20.5 mmol) in THF (250 mL) was heated at reflux for 4 h. After cooling to room temperature, the mixture was diluted with EtOAc (500 mL) and washed with water (100 mL) and brine (100 mL). The organic solution was dried over MgSO$_4$, filtered and concentrated. The residue was purified by flash chromatography (SiO$_2$; 10% EtOH/CH$_2$Cl$_2$) to give 5.66 g (85%) of the enone adduct 2-2 as a tan solid. $^1$H NMR (400.13 MHz, CDCl$_3$): δ8.77 (s, 2H), 7.42 (d, J=16.3 Hz, 1H), 7.04 (d, J =7.3 Hz, 1H), 6.80 (d, J=16.3 Hz, 1H), 6.34 (d, J=7.3 Hz, 1H) 4.80 (br s, 1H), 3.38 (m, 2H), 2.76 (s, 3H), 2.70–2.65 (om, 4H), 2.57 (m, 2H), 1.88 (m, 2H), 1.74–1.70 (om, 4H) ppm. $^{13}$C NMR (100.61 MHz, CDCl$_3$): δ199.5, 169.4, 158.0, 156.0, 155.9, 136.8, 135.1, 128.4, 125.5, 113.4, 111.5, 41.8, 41.4, 37.7, 29.5, 26.5, 26.2, 24.0, 21.6 ppm.

Step C: (R or S) and (S or R)-1-(2-Methyl-pyrimidin-5-yl)-7-(5,6,7,8-tetrahydro-[1,8]-naphthyridin-2-yl)-hept-1-en-3-ol (2–3a and 2–3b)

Enone 2-2 (7.13 g, 22.0 mmol) was dissolved in MeOH (200 mL) and cooled to 0° C. Solid NaBH$_4$ (1.00 g, 1.2 eq) was added in 3 portions. After 15 minutes of stirring, the reaction was quenched with 10% aqueous citric acid, and 1 N HCl was added to adjust the pH to about 3. The mixture was stirred for 20 min., and then 1N NaOH was added to adjust the pH to about 9. Methanol was removed in vacuo and the residue was extracted with CHCl$_3$ (3×100 mL). The combined organic extracts were dried over MgSO$_4$, filtered, and concentrated. The residue was purified by flash chromatography (SiO$_2$; 80:10:10 CHCl$_3$/MeOH/EtOAc) to give 6.10 g (85%) of the racemic allylic alcohol 2-3 as a pale yellow solid. The racemic mixture was resolved by chiral preparative HPLC (10×50 cm Chiralpak AD column, 80/20 EtOH/Hexanes+0.1% diethylamine; 6.1 g injection @ 300 mL/min) to give 2.72 gm (38%) of the first eluting enantiomer 2–3a (R$_T$=40 to 51 min; >98% enantiomeric excess) and 2.1 g (34%) of the second eluting enantiomer 2–3b (R$_T$=51 to 62 min).

Step D: 3(R or S)-(2-Methylpyrimidin-5-yl)-9-(5,6,7,8-tetrahydro-[1,8] naphthyridin-2-yl)-non-4-enoic acid ethyl ester (2–4a)

To a stirred solution of allylic alcohol 2–3a (4.7 g, 13.9 mmol) in triethyl orthoacetate (88 mL) was added a solution of propionic acid (5.34 mL of a 0.15 M soln in (EtO)$_3$CMe; 0.80 mmol). The solution was heated to reflux (145° C.) for 2 hours. The solution was then cooled to room temperature and the reaction treated with 1 N HCl/brine (25 mL). After stirring for 10 min, the mixture was neutralized and extracted with EtOAc (3×100 mL) and the combined organic extracts dried over MgSO$_4$, filtered and concentrated. The residue was purified by flash chromatography (SiO$_2$; 80:10:10 CHCl$_3$/EtOAc/MeOH) to give 4.6 g (82%) of 2–4a as a brown oil. $^1$H NMR (300 MHz, CDCl$_3$): δ8.52 (s, 2H), 7.04 (d, J=7.3 Hz, 1H), 6.34 (d, J=7.3 Hz, 1H), 5.53 (m, 2H), 5.05 (br s, 1H), 4.07 (q, J=7.0 Hz, 2H), 3.81 (m, 1H), 3.49 (s, 3H), 2.69 (m, 3H), 2.58 (m, 3H), 2.05 (m, 2H), 1.90 (m, 2H), 1.63 (m, 2H), 1.41 (m, 2H), 1.18 (t, J=7.0 Hz, 3H) ppm.

Step E: 3(R or S)-(2-Methylpyrimidin-5-yl)-9-(5,6,7,8-tetrahydro-[1,8]naphthyridin-2-yl)-nonanoic acid ethyl ester (2–5a)

Unsaturated ester 2–4a (12.3 g, 30.1 mmol) was dissolved in ethanol (300 mL) and the solution purged with argon gas for 20 min. 10% Palladium-on-carbon (3.2 g) was added. A balloon of hydrogen gas was affixed to the partially evacuated flask. The heterogeneous reaction was stirred for 3.5 h. The reaction mixture was then filtered through Celite, and the filtrate concentrated. The residue was purified by flash chromatography (SiO$_2$; 80:10:10 CHCl$_3$/MeOH/EtOAc) to give 10.2 g (83%) of ester 2–5a as a colorless oil. $^1$H NMR (400 MHz, CDCl$_3$):δ8.43 (s, 2H), 7.04 (d, J=7.2 Hz, 1H), 6.27 (d, J=7.2 Hz, 1H), 4.01 (q, J=7.1 Hz, 2H), 3.37 (m, 2H), 3.01 (m, 1H), 2.64 (m, 3H), 2.68 (s, 3H), 2.48 (m, 3H), 1.87 (m, 2H), 1.59 (m, 3H), 1.24 (m, 3H), 1.12 (t, J=7.1 Hz, 3H) ppm.

Step F: 3(R or S)-(2-Methylpyrimidin-5-yl)-9-(5,6,7,8-tetrahydro-[1,8]naphthyridin-2-yl)-nonanoic acid (2–6a)

To a stirred solution of ester 2–5a (10.2 g, 24.8 mmol) in MeOH/THF (50 mL/150 mL) was added 1N NaOH (75 mL, 75 mmol). The reaction was stirred for 16 h at room temperature and then neutralized with 1N HCl (75 mL). The solvent was removed in vacuo. The residue was purified by flash chromatography (SiO$_2$; 80:10:10 CHCl$_3$/MeOH/EtOAc) to give a viscous foam which was redissolved in a minimal volume of water to produce a white gummy paste. Stirring and scratching with a metal spatula produced a white crystalline solid. The precipitate was collected by filtration to give 8.0 g (84%) of the zwitterion 2–6a. $^1$H NMR (400 MHz, CD$_3$OD): δ 8.54 (s, 2H), 7.36 (d, J=7.2 Hz, 1H), 6.43 (d, J= 7.2 Hz, 1H), 3.39 (t, J=8.0 Hz, 2H), 3.27 (s, 3H), 3.12 (m, 1H), 2.72 (t, J=6.0 Hz, 2H), 2.58 (m, 4H), 1.87 (m, 2H), 1.76 (m, 1H), 1.61 (m, 3H), 1.41 (m, 1H), 1.29 (m, 5H) ppm.

Figure 3:
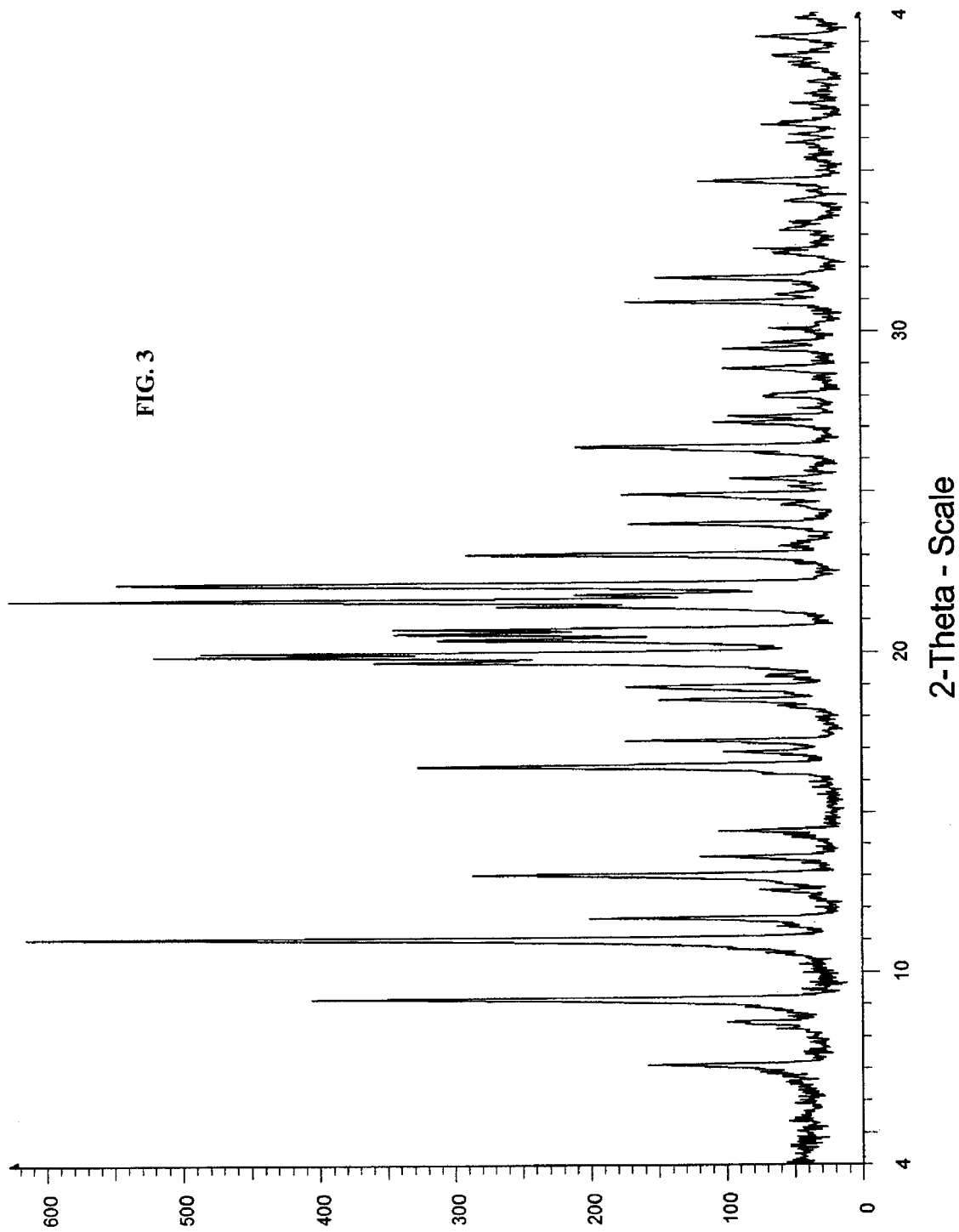
FIG. 3 is a characteristic X-ray diffraction pattern of the crystalline zwitterion trihydrate of structural formula (IV).

The X-ray powder diffraction pattern of the crystalline zwitterion trihydrate is illustrated in FIG. 3. It has characteristic diffraction peaks corresponding to d-spacings of 9.69, 8.04, 7.60, 6.80, 5.39, 4.51, 4.47, 4.44, 4.35, 4.32, 4.29, 4.11, 4.02, and 3.86 angstroms.

Figure 6:
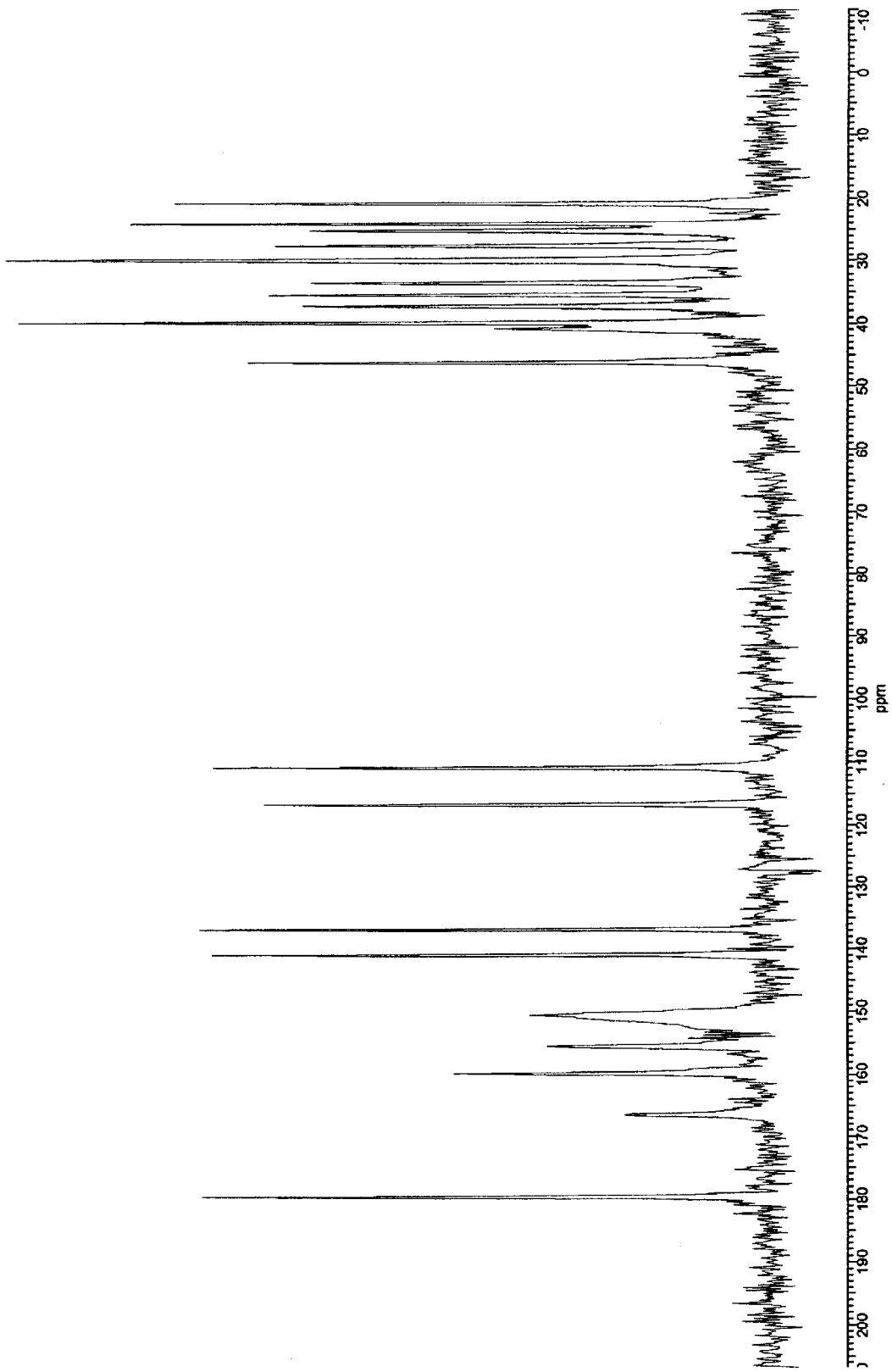
FIG. 6 is a carbon-13 cross-polarization magic-angle spinning (CPMAS) nuclear magnetic resonance (NMR) spectrum of the crystalline zwitterion trihydrate of structural formula (IV).

The crystalline zwitterion trihydrate was also characterized by solid-state carbon-13 NMR spectroscopy. FIG. 6 illustrates the carbon-13 CPMAS NMR spectrum of the crystalline zwitterion trihydrate which exhibits signals with chemical shift values at 179.5, 166.4, 159.7, 155.4, 150.5, 140.9, 136.8, 116.6, 110.8, 46.0, 39.7, 37.2, 35.5, 33.4, 29.8, 27.4, 25.1, 24.1, and 20.7 ppm.

Figure 9:
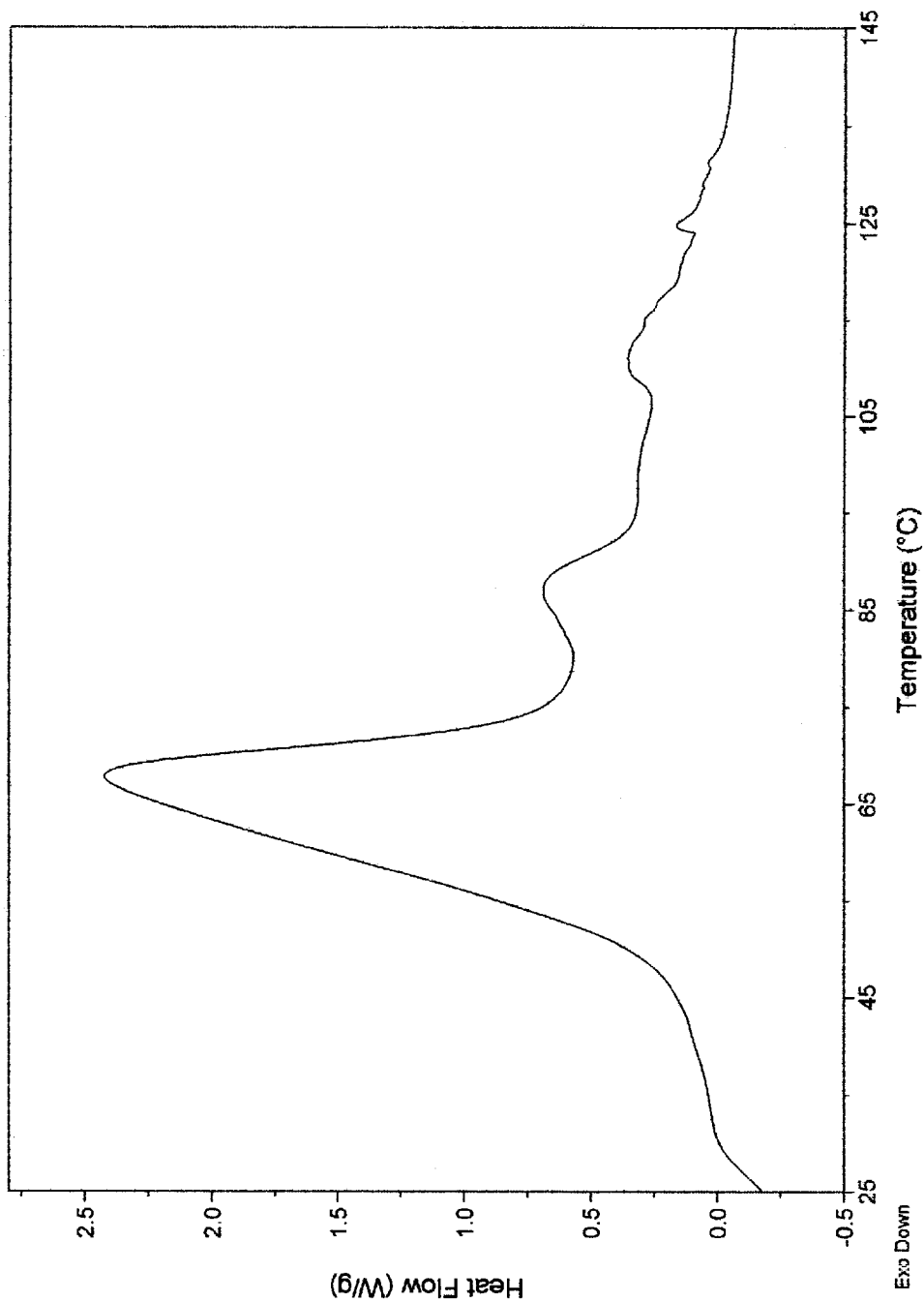
FIG. 9 is a differential scanning calorimetric (DSC) curve of the crystalline zwitterion trihydrate of structural formula (IV).

The differential scanning calorimeter (DSC) curve of the crystalline zwitterion trihydrate is illustrated in FIG. 9. The DSC curve exhibits a broad dehydration endothermic peak centered around 68° C. (extrapolated onset temperature of about 50° C.). The small endothermic peak (peak temperature at about 87° C.) on the shoulder of the dehydration endotherm is likely attributed to degradation of the salt.

Figure 12:
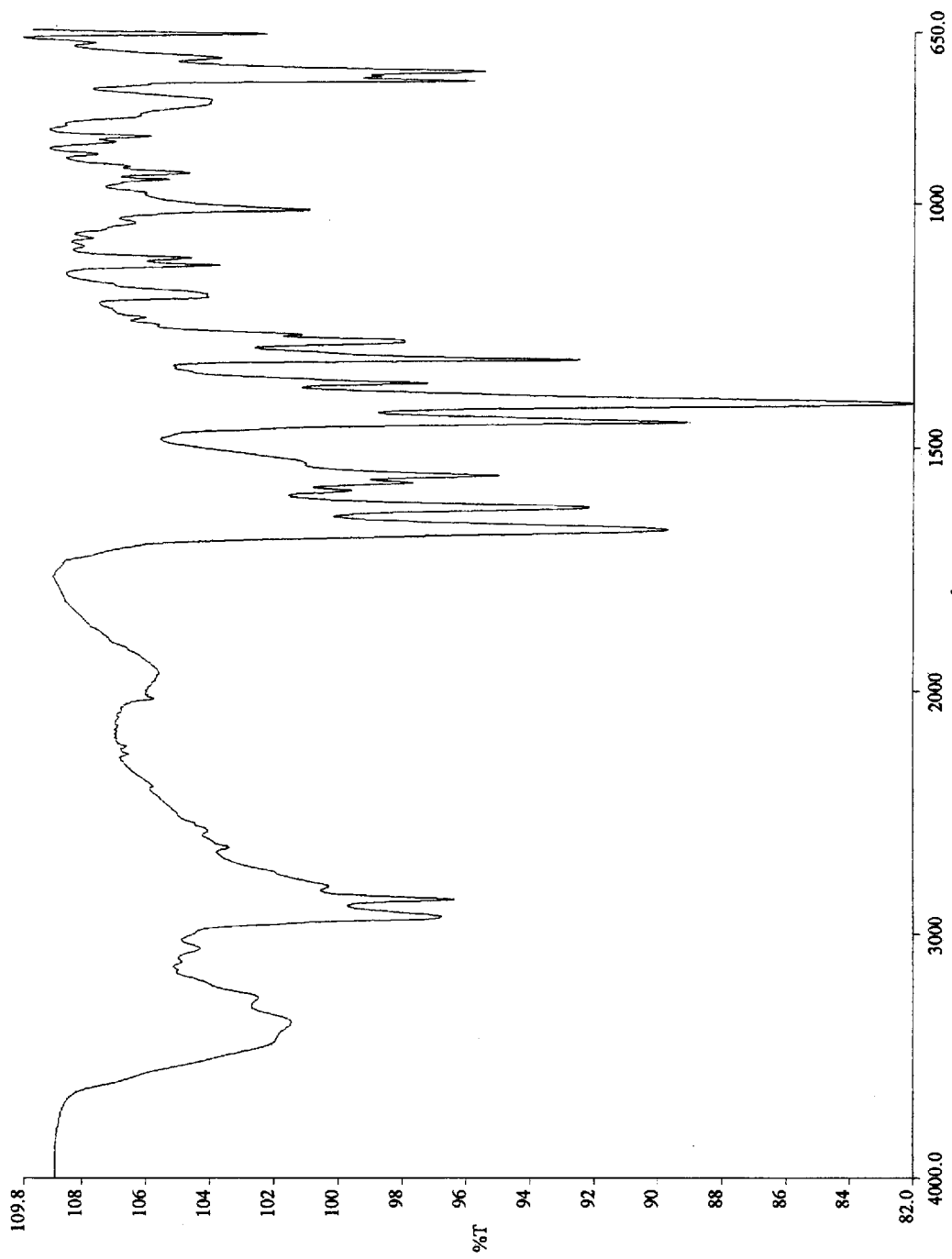
FIG. 12 is an FT infrared spectrum of the crystalline zwitterion trihydrate of structural formula (IV).

The FT infrared spectrum of the crystalline zwitterion trihydrate is illustrated in FIG. 12, which exhibits significant absorption bands at 1671, 1624, 1559, 1450, 1409, 1322, 1288, 1016, 752, and 733 cm$^{-1}$.

The content of water as obtained with Karl-Fischer titration was 12.5 wt % (the theory for a trihydrate is 12.4 wt %).

Step G: 3(R or S)-(2-Methylpyrimidin-5-yl)-9-(5,6,7,8-tetrahydro-[1,8]naphthyridin-2-yl)-nonanoic acid tris(hydroxymethyl)aminomethane salt (2–7a)

The product from Step F (2–6a) (8.73 g, 20.0 mmol), tris(hydroxymethyl)aminomethane (2.42 g, 20.0 mmol), and methanol (100 mL) were added to a 500 mL flask. The mixture was warmed to 30° C. to obtain complete solution. Ethyl acetate (100 mL) was added and the mixture seeded with crystals of the authentic "tris" salt (2 mg). The slurry was aged 30 minutes and then concentrated at constant volume (25–30° C., 100 mmHg) by adding ethyl acetate (total of 100 mL). The resultant slurry was cooled to 20° C., aged for one hour, and filtered. The product 2–7a was washed with ethyl acetate (50 mL) and dried in vacuo at 20° C.

The X-ray powder diffraction pattern of the crystalline tris(hydroxymethyl)aminomethane ("tris") salt [R$^1$=H; R$^2$=C(CH$_2$OH)$_3$] is illustrated in FIG. 1. It has characteristic diffraction peaks corresponding to d-spacings of 16.07, 8.52, 5.70, 5.35, 4.51, 4.28, 4.01, 3.81, 3.56, 3.41, and 3.21 angstroms.

Figure 4:
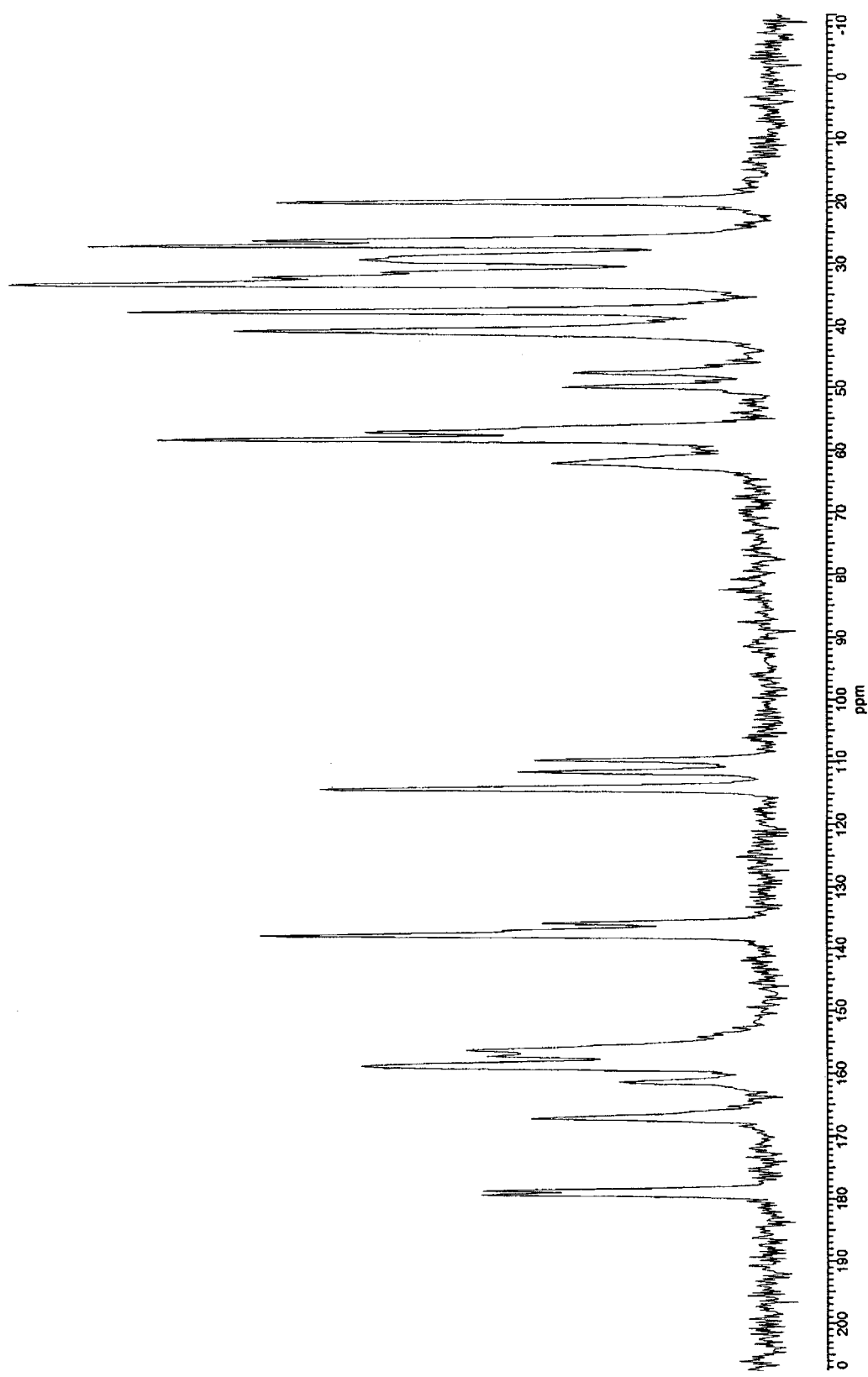
FIG. 4 is a carbon-13 cross-polarization magic-angle spinning (CPMAS) nuclear magnetic resonance (NMR) spectrum of the crystalline salt of structural formula I wherein $R^1$ is hydrogen and $R^2$ is $C(CH_2OH)_3$.

The crystalline "tris" salt was also characterized by solid-state NMR spectroscopy. FIG. 4 illustrates the carbon-13 CPMAS NMR spectrum of the crystalline salt which exhibits signals with chemical shift values at 179.0, 178.5, 166.9, 161.2, 158.5, 157.1, 156.1, 137.6, 135.8, 114.0, 111.4, 109.5, 62.0, 58.0, 57.0, 49.8, 47.4, 40.5, 37.4, 32.9, 29.1, 26.8, 26.0, and 19.9 ppm.

Figure 7:
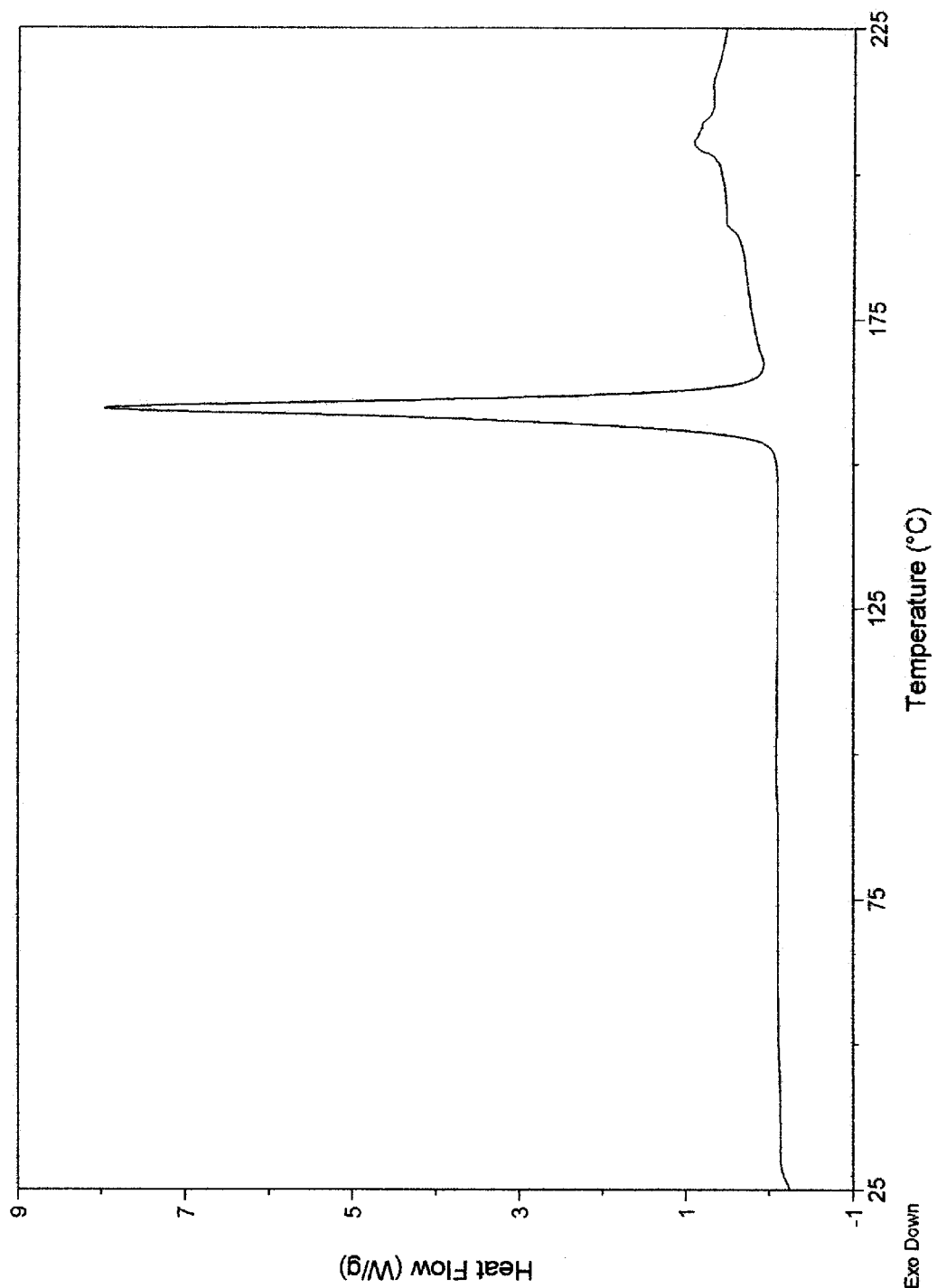
FIG. 7 is a differential scanning calorimetric (DSC) curve of the crystalline salt of Formula I wherein $R^1$ is hydrogen and $R^2$ is $C(CH_2OH)_3$.

The differential scanning calorimeter (DSC) curve of the crystalline anhydrous "tris" salt is illustrated in FIG. 7. The DSC curve exhibits a melting/decomposition endotherm with a peak temperature of about 160° C. (extrapolated onset temperature of about 155° C.).

Figure 10:
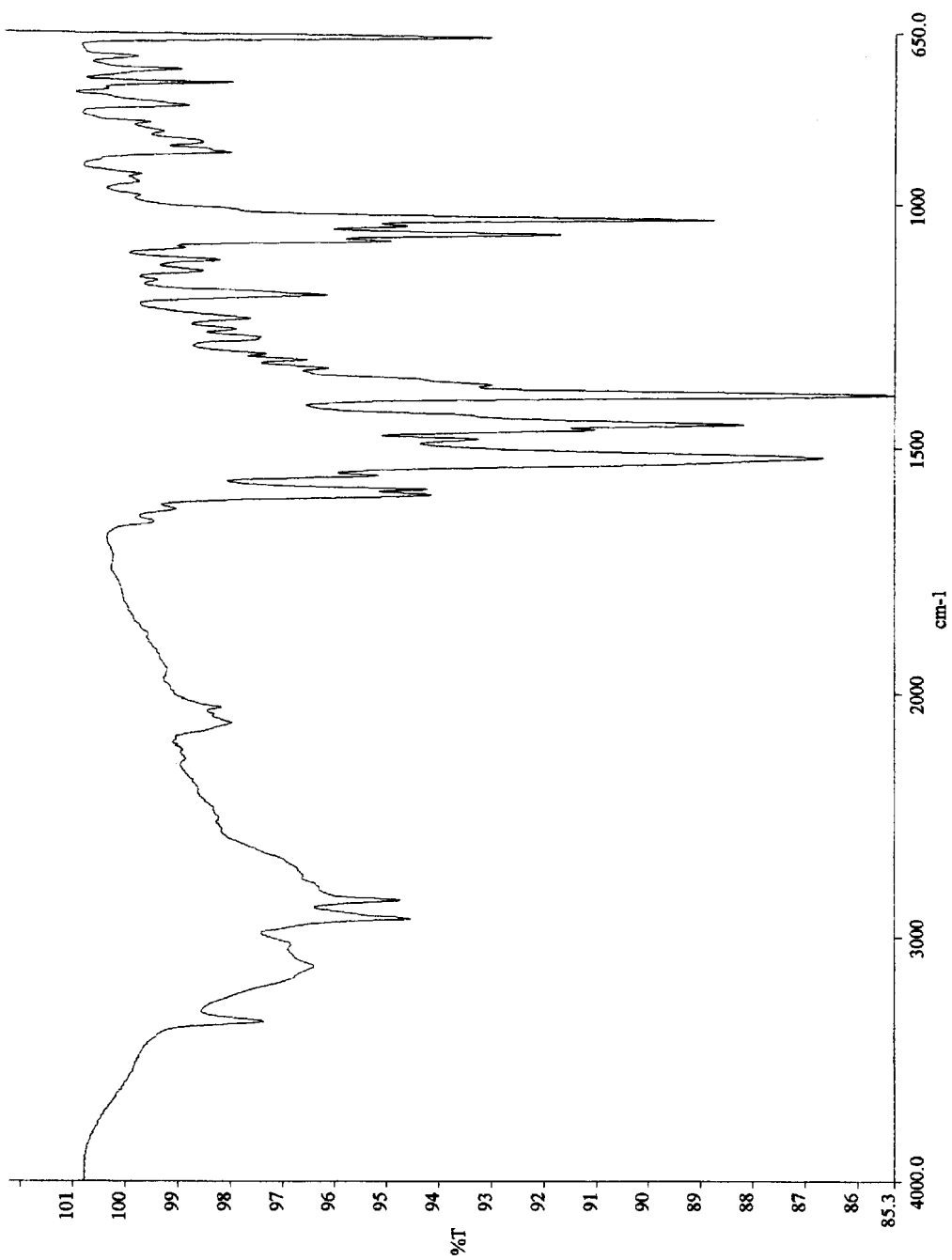
FIG. 10 is an FT infrared spectrum (FT-IR) of the crystalline salt of structural formula I wherein $R^1$ is hydrogen and $R^2$ is $C(CH_2OH)_3$.

The FT infrared spectrum of the crystalline anhydrous "tris" salt is illustrated in FIG. 10, which exhibits significant absorption bands at 3347, 1597, 1586, 1519, 1452, 1392, 1062, and 1031 cm$^{-1}$.

The content of water as obtained with Karl-Fischer titration was about 0.3wt %.

EXAMPLE 2

3(S or R)-(2-Methylpyrimidin-5-yl)-9-(5,6,7,8-tetrahydro-[1,8]naphthyridin-2-yl)-nonanoic acid tris(hydroxymethyl)aminomethane salt (2–7b)

The enantiomeric "tris" salt 2–7b was prepared from 2–3b as described for 2–7a.

EXAMPLE 3

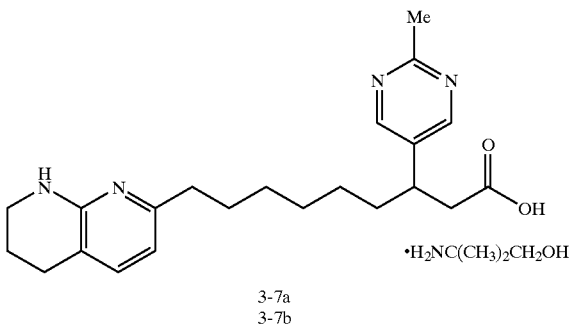

3-7a
3-7b

3(R or S)-(2-Methylpyrimidin-5-yl)-9-(5,6,7,8-tetrahydro-[1,8]naphthyridin-2-yl)-nonanoic acid 2-amino-2-methyl-1-propanol salt (3–7a)

Compound 2–6a (1.0 g, 2.29 mmol), 2-amino-2-methyl-1-propanol (2.29 mmol), and methanol (2 mL) were added to a 25 mL flask. The mixture was warmed to 30° C. to obtain complete solution. Ethyl acetate (20 mL) was added and the mixture stirred at 20° C. to obtain a slurry. The slurry was aged 60 minutes and filtered. The product was washed with ethyl acetate (5 mL) and dried in vacuo at 20° C.

Figure 2:
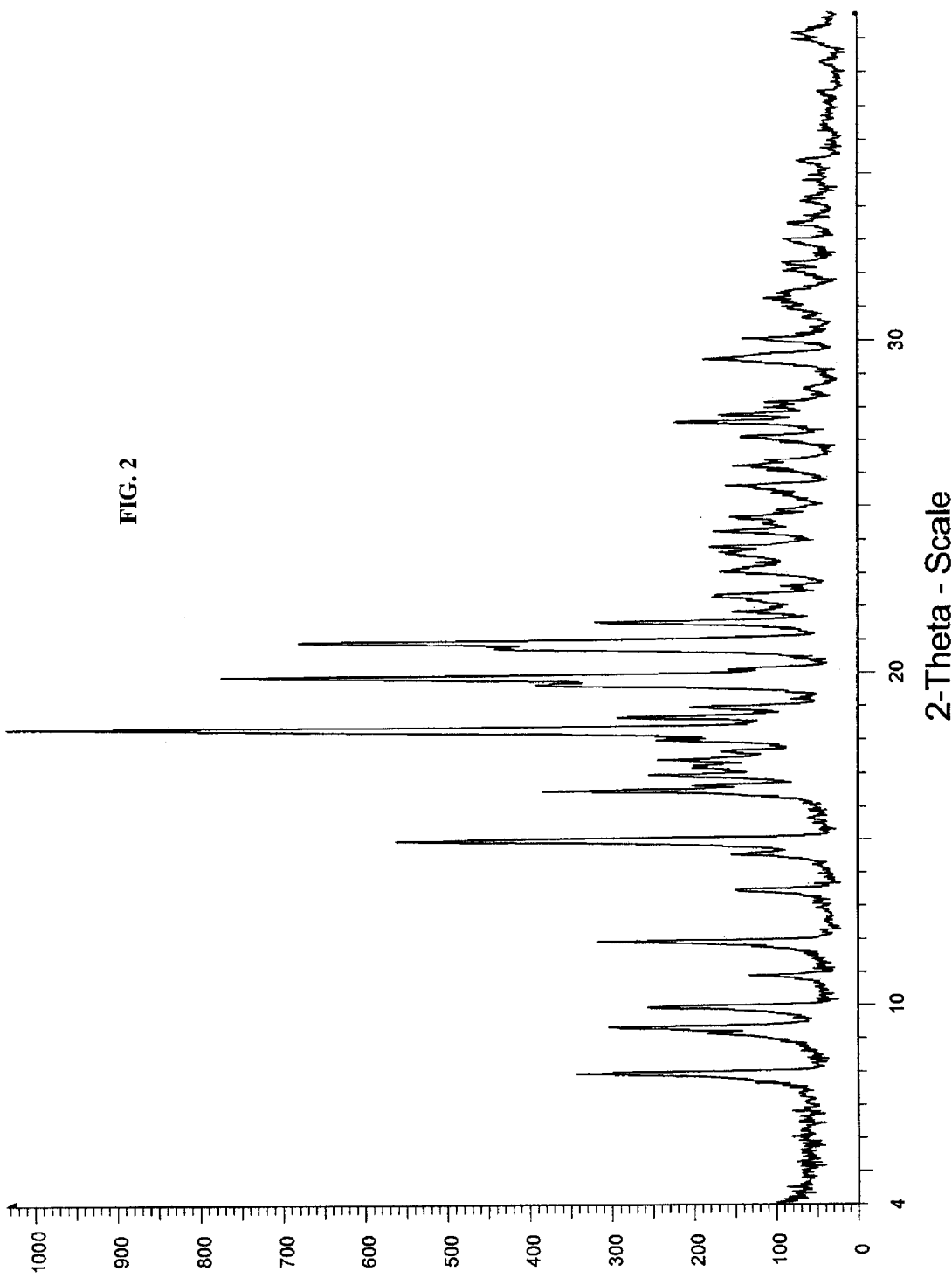
FIG. 2 is a characteristic X-ray diffraction pattern of the crystalline salt of structural formula I wherein $R^1$ is hydrogen and $R^2$ is $C(CH_3)_2CH_2OH$.

The X-ray powder diffraction pattern of the crystalline 2-amino-2-methyl-1-propanol salt [$R^1$=H; $R^2$=C($CH_3$)$_2$$CH_2$OH] is illustrated in FIG. 2. It has characteristic diffraction peaks corresponding to d-spacings of 11.17, 9.51, 8.92, 7.44, 5.92, 5.38, 4.84, 4.46, 4.24, and 4.13 angstroms.

Figure 5:
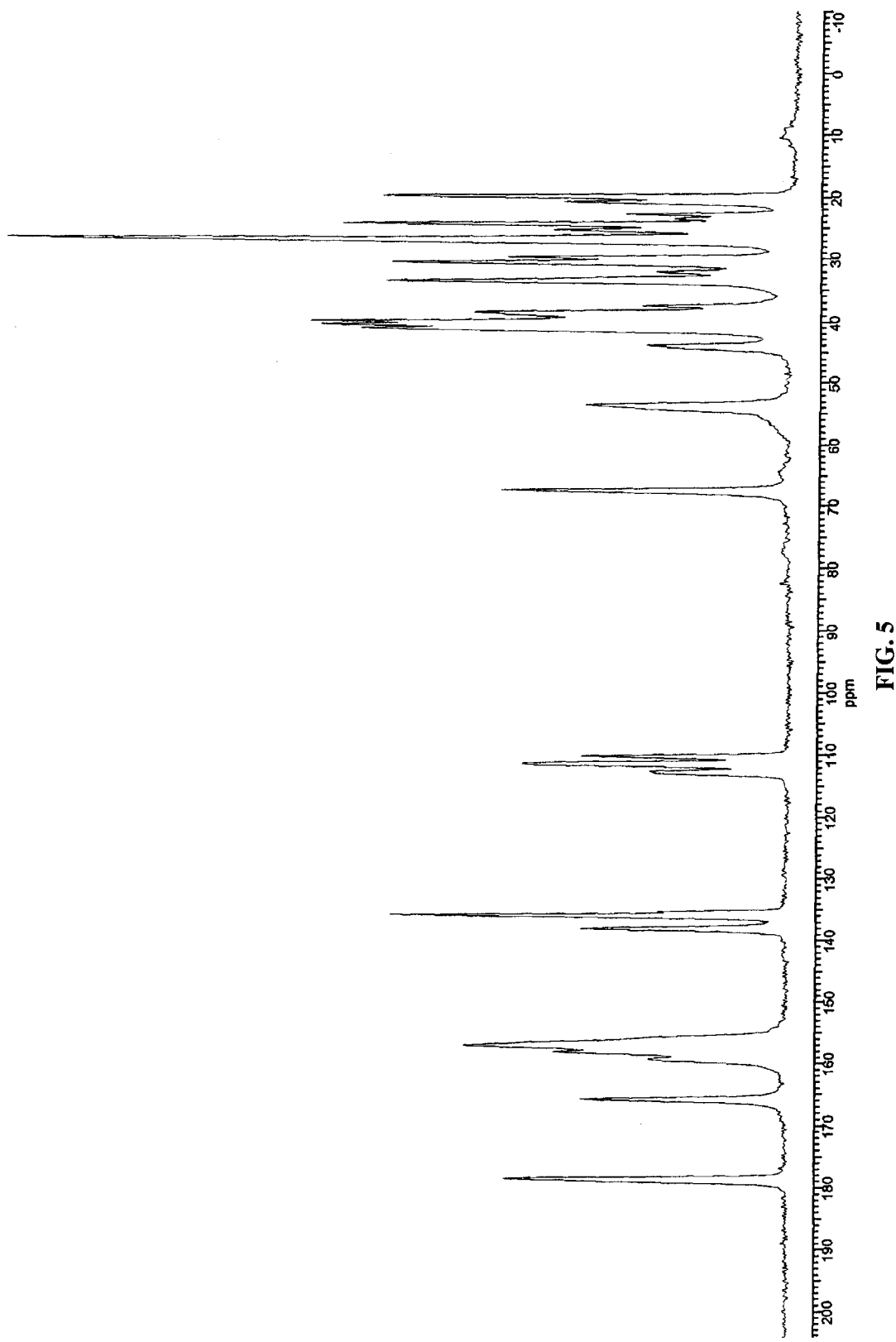
FIG. 5 is a carbon-13 cross-polarization magic-angle spinning (CPMAS) nuclear magnetic resonance (NMR) spectrum of the crystalline salt of structural formula I wherein $R^1$ is hydrogen and $R^2$ is $C(CH_3)_2CH_2OH$.

The crystalline 2-amino-2-methyl-1-propanol salt was also characterized by solid-state NMR spectroscopy. FIG. 5 illustrates the carbon-13 CPMAS NMR spectrum of the crystalline salt, which exhibits signals with chemical shift values at 178.7, 165.9, 159.3, 158.2, 157.2, 138.1, 136.1, 112.8, 111.6, 110.3, 67.6, 53.7, 44.1, 41.2, 40.5, 40.1, 38.7, 37.6, 33.6, 32.1, 30.7, 29.9, 27.0, 25.4, 24.5, 22.9, 20.8, and 19.9 ppm.

Figure 8:
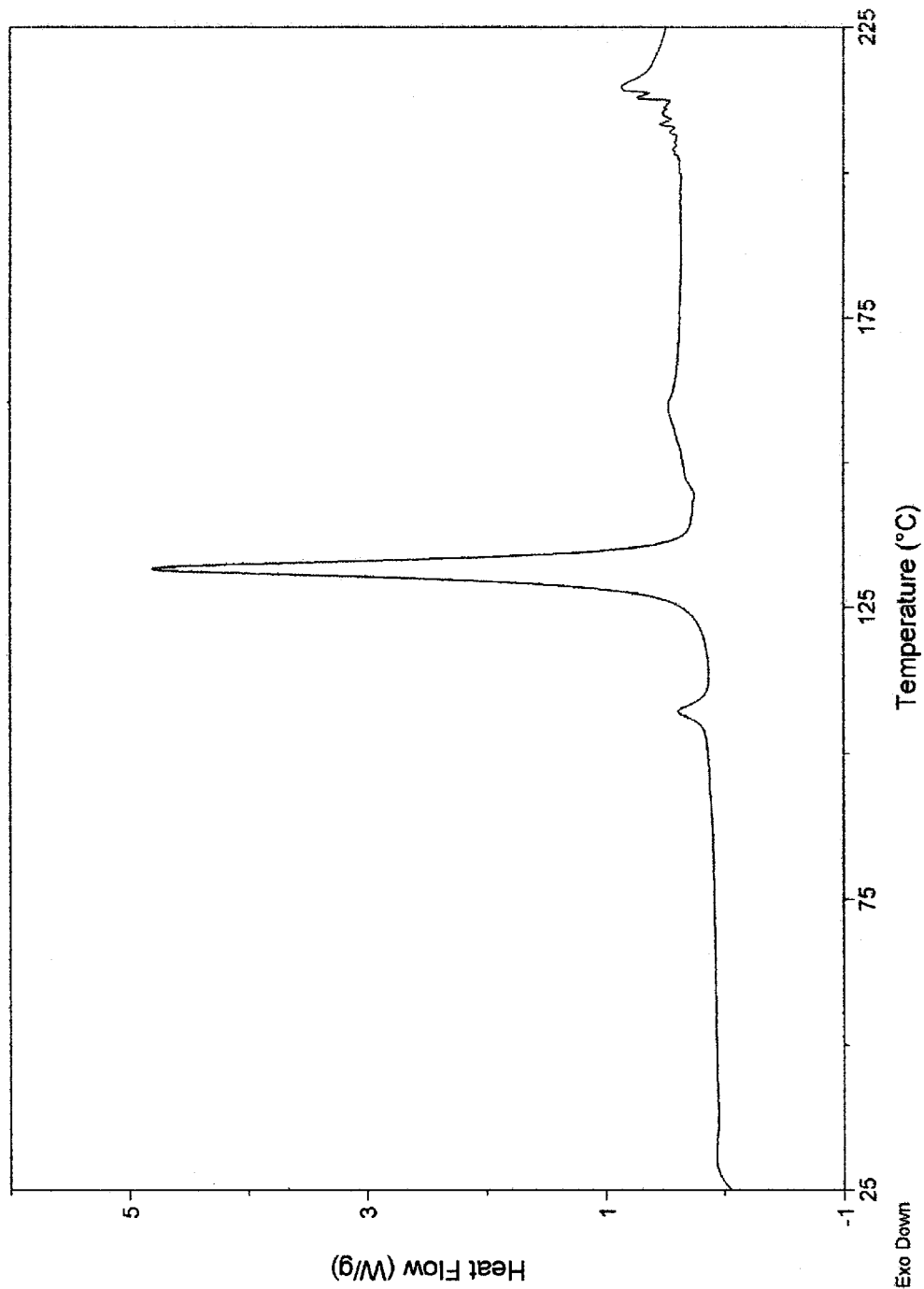
FIG. 8 is a differential scanning calorimetric (DSC) curve of the crystalline salt of Formula I wherein $R^1$ is hydrogen and $R^2$ is $C(CH_3)_2CH_2OH$.

The differential scanning calorimeter (DSC) curve of the crystalline anhydrous 2-amino-2-methyl-1-propanol salt is illustrated in FIG. 8. The DSC curve exhibits a melting/decomposition endotherm with a peak temperature of about 133° C. (extrapolated onset temperature of about 126° C.). A small reversible endothermic peak with a peak temperature of 107° C. is also observed.

Figure 11:
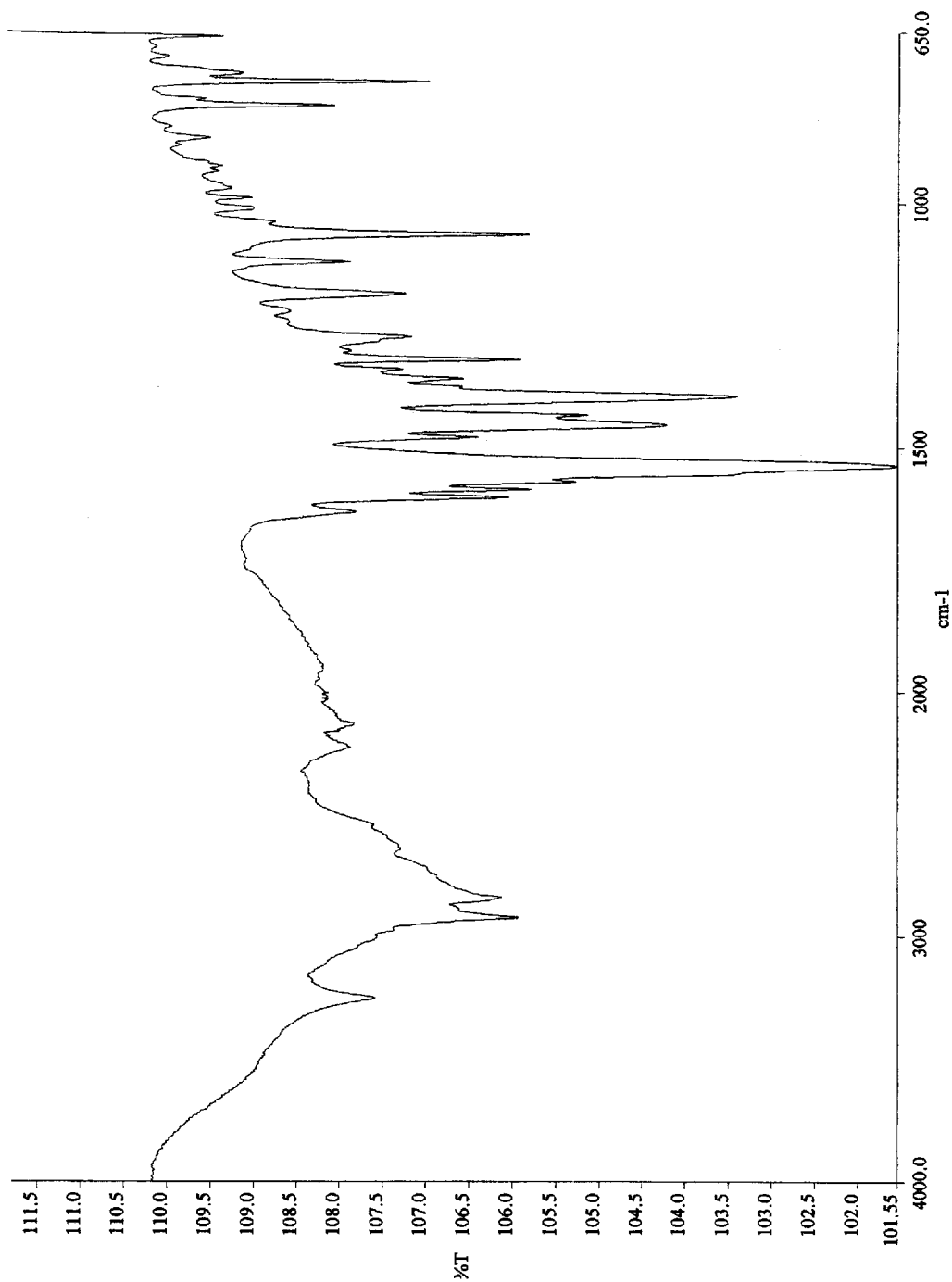
FIG. 11 is an FT infrared spectrum of the crystalline salt of structural formula I wherein $R^1$ is hydrogen and $R^2$ is $C(CH_3)_2CH_2OH$.

The FT infrared spectrum of the crystalline anhydrous 2-amino-2-methyl-1-propanol salt is illustrated in FIG. 11, which exhibits significant absorption bands at 3252, 1537, 1454, 1394, 1320, 1064, 802, and 751 cm$^{-1}$.

The content of water as obtained with Karl-Fischer titration was about 0.3wt %.

EXAMPLE 4

3(S or R)-(2-Methylpyrimidin-5-yl)-9-(5,6,7,8-tetrahydro-[1,8]naphthyridin-2-yl)-nonanoic acid 2-amino-2-methyl-1-propanol salt (3–7b)

The enantiomeric 2-amino-2-methyl-1-propanol salt 3–7b was prepared from 2–3b as described for 2–7a.

EXAMPLES OF PHARMACEUTICAL FORMULATIONS

The amine salts of formula formula I can be formulated into a tablet by a direct compression process. A 100 mg potency tablet is composed of 100 mg of the active ingredient, 276 mg mannitol, 20 mg of croscarmellose sodium, and 4 mg of magnesium stearate. The active ingredient, microcrystalline cellulose, and croscarmellose are first blended, and the mixture is then lubricated with magnesium stearate and pressed into tablets.

An intravenous (i.v.) aqueous formulation is prepared by dissolving an amine salt of structural formula I in ethanol (10%)/water (90%). For a formulation with a concentration of 5 mg/mL, 5 mg of the active ingredient is dissolved in one mL ethanol (10%)/water (90%) solution.

What is claimed is:

1. An amine salt of 3-(2-methyl-pyrimidin-5-yl)-9-(5,6,7,8-tetrahydro-[1,8]-naphthyridin-2-yl)-nonanoic acid of structural formula I:

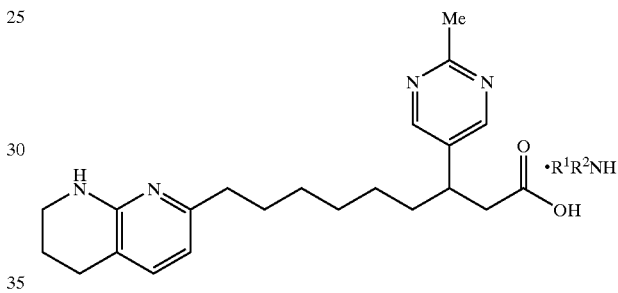

or a pharmaceutically acceptable hydrate thereof, wherein $R^1$ and $R^2$ are both hydrogen, $R^1$ is hydrogen and $R^2$ is C(CH$_2$OH)$_3$, $R^1$ is hydrogen and $R^2$ is C(CH$_3$)$_2$CH$_2$OH, $R^1$ is hydrogen and $R^2$ is CH$_2$CH$_2$NH$_2$, or $R^1$ is CH$_2$C$_6$H$_5$ and $R^2$ is CH$_2$CH$_2$C$_6$H$_5$.

2. The salt of claim 1 of structural formula II having the (S)-configuration at the chiral center marked with an *

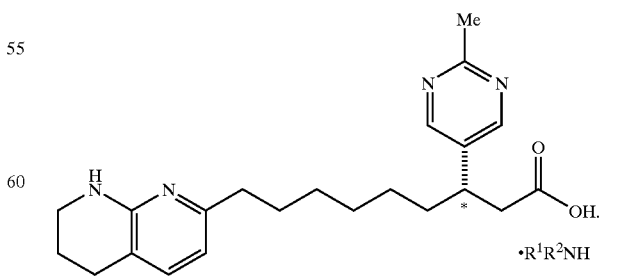

3. The salt of claim 1 of structural formula III having the (R)-configuration at the chiral center marked with an *

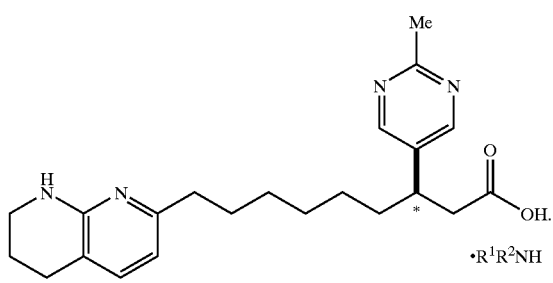

(III)

4. The salt of claim 1 wherein $R^1$ is hydrogen and $R^2$ is $C(CH_2OH)_3$.

5. The salt of claim 1 wherein $R^1$ is hydrogen and $R^2$ is $C(CH_3)_2CH_2OH$.

6. The salt of claim 2 wherein $R^1$ is hydrogen and $R^2$ is $C(CH_2OH)_3$.

7. The crystalline salt of claim 4 characterized by an X-ray powder diffraction pattern showing diffraction peaks corresponding to d-spacings of 16.07, 8.52, 5.70, 5.35, 4.51, 4.28, 4.01, 3.81, 3.56, 3.41, and 3.21 angstroms.

8. The crystalline salt of claim 4 characterized by a solid-state carbon-13 CPMAS nuclear magnetic resonance spectrum showing signals at 179.0, 178.5, 166.9, 161.2, 158.5, 157.1, 156.1, 137.6, 135.8, 114.0, 111.4, 109.5, 62.0, 58.0, 57.0, 49.8, 47.4, 40.5, 37.4, 32.9, 29.1, 26.8, 26.0, and 19.9 ppm.

9. The crystalline salt of claim 4 characterized by an FT-infrared spectrum showing significant absorption bands at 3347, 1597, 1586, 1519, 1452, 1392, 1062, and 1031 $cm^{-1}$.

10. A salt comprising the ions of 3-(2-methyl-pyrimidin-5-yl)-9-(5,6,7,8-tetrahydro-[1,8]-naphthyridin-2-yl)-nonanoic acid anion and protonated tris(hydroxymethyl) aminomethane cation.

11. A salt comprising the ions of 3-(2-methyl-pyrimidin-5-yl)-9-(5,6,7,8-tetrahydro-[1,8]-naphthyridin-2-yl)-nonanoic acid anion and protonated 2-amino-2-methyl-1-propanol cation.

12. A pharmaceutical composition comprising a prophylactically or therapeutically effective amount of the salt according to claim 1 or a pharmaceutically acceptable hydrate thereof in association with one or more pharmaceutically acceptable carriers.

13. A method for the prevention and/or treatment of osteoporosis comprising administering to a patient in need of such prevention or treatment a prophylactically or therapeutically effective amount of the salt according to claim 1, or a pharmaceutically acceptable hydrate thereof.

14. A process for preparing the amine salt of claim 1 comprising the step of contacting one molar equivalent of 3-(2-methyl-pyrimidin-5-yl)-9-(5,6,7,8-tetrahydro-[1,8]-naphthyridin-2-yl)-nonanoic acid in an organic solvent with about a one molar equivalent of an amine $R^1R^2NH$ wherein $R^1$ and $R^2$ are both hydrogen, $R^1$ is hydrogen and $R^2$ is $C(CH_2OH)3$, $R^1$ is hydrogen and $R^2$ is $C(CH_3)_2CH_2OH$, $R^1$ is hydrogen and $R^2$ is $CH_2CH_2NH_2$, or $R^1$ is $CH_2C_6H_5$ and $R^2$ is $CH_2CH_2C_6H_5$;

at a temperature in the range of about 0° C. to 100° C.

15. The process of claim 14 wherein said organic solvent is a $C_1$–$C_4$ linear or branched alkanol.

* * * * *